(12) United States Patent
Suzuki et al.

(10) Patent No.: US 8,404,793 B2
(45) Date of Patent: Mar. 26, 2013

(54) ALLERGEN SUPPRESSOR, ALLERGEN-SUPPRESSION PROCESSED FIBER AND METHOD OF PRODUCING THE SAME

(75) Inventors: Taro Suzuki, Mishima-gun (JP); Mitsuhito Teramoto, Mishima-gun (JP); Akihiko Fujiwara, Mishima-gun (JP)

(73) Assignee: Sekisui Chemical Co., Ltd., Osaka (JP)

( * ) Notice: Subject to any disclaimer, the term of this patent is extended or adjusted under 35 U.S.C. 154(b) by 782 days.

(21) Appl. No.: 10/585,305

(22) PCT Filed: Jan. 7, 2004

(86) PCT No.: PCT/JP2004/000017
§ 371 (c)(1),
(2), (4) Date: Sep. 27, 2006

(87) PCT Pub. No.: WO2005/066410
PCT Pub. Date: Jul. 21, 2005

(65) Prior Publication Data
US 2007/0160567 A1    Jul. 12, 2007

(51) Int. Cl.
*A61K 31/787* (2006.01)
*A61K 31/74* (2006.01)
*A61K 31/715* (2006.01)

(52) U.S. Cl. ............. 526/329; 424/78.27; 424/78.3; 424/171.1

(58) Field of Classification Search ............ 514/183
See application file for complete search history.

(56) References Cited

U.S. PATENT DOCUMENTS

| | | | | |
|---|---|---|---|---|
| 2,844,557 | A * | 7/1958 | Welch | 523/406 |
| 5,985,814 | A * | 11/1999 | Zocchi et al. | 510/280 |
| 2002/0182184 | A1* | 12/2002 | Pearl et al. | 424/93.4 |
| 2003/0152528 | A1* | 8/2003 | Singh et al. | 424/53 |
| 2005/0197319 | A1* | 9/2005 | Nonomura et al. | 514/57 |

FOREIGN PATENT DOCUMENTS

| | | |
|---|---|---|
| GB | 2 058 820 A | 4/1981 |
| JP | 56-49080 A | 5/1981 |
| JP | SHO-56-049080 | 5/1981 |
| JP | SHO-61-044821 | 3/1986 |
| JP | SHO-62-078266 | 4/1987 |
| JP | SHO-62-213707 | 9/1987 |
| JP | HEI-05-320015 | 12/1993 |
| JP | HEI-07-032735 | 4/1995 |
| JP | 7-171387 A | 7/1995 |
| JP | HEI-07-171387 | 7/1995 |
| JP | HEI-09-059877 | 3/1997 |
| JP | HEI-09-158042 | 6/1997 |
| JP | 2000-191410 | 7/2000 |
| JP | 2000-204182 | 7/2000 |
| JP | 2001-214367 A | 8/2001 |
| JP | 2002-326944 | 11/2002 |
| JP | 2003-082581 | 3/2003 |
| JP | 2003-82581 A | 3/2003 |
| JP | 2003-093209 | 4/2003 |
| JP | 2003-93209 A | 4/2003 |
| JP | 2003-096670 | 4/2003 |
| JP | 2003-96670 A | 4/2003 |
| JP | 2003-313778 | 11/2003 |
| JP | 2003-313778 A | 11/2003 |
| JP | 2004-003040 | 1/2004 |
| JP | 2004-3040 A | 1/2004 |

OTHER PUBLICATIONS

Office Action Dated Dec. 4, 2009 in a counterpart European Application No. 04700508.7.
Office Action for Counterpart EP 04700508.7, Issued on May 3, 2012.

* cited by examiner

*Primary Examiner* — Walter Webb
(74) *Attorney, Agent, or Firm* — Novak Druce Connolly Bove + Quigg LLP

(57) ABSTRACT

It is an object of the present invention to provide an allergen suppressor exerting an effect of suppressing an allergen under humidities normally used, and an allergen-suppression processed fiber, which can suppress an allergen adhering to fibers automatically without applying an allergen-suppression process and a method of producing the same.

That is, the present invention is an allergen suppressor, which contains a hydrophilic polymer and a component suppressing an allergen.

5 Claims, No Drawings

ALLERGEN SUPPRESSOR, ALLERGEN-SUPPRESSION PROCESSED FIBER AND METHOD OF PRODUCING THE SAME

CROSS-REFERENCE TO RELATED APPLICATION

This application is a 371 of PCT/JP2004/000017, filed Jan. 7, 2004, the disclosure of which is incorporated herein by reference.

TECHNICAL FIELD

The present invention relates to an allergen suppressor which can suppress the allergens of mites, pollens or the like, and an allergen-suppression processed fiber, which can suppress allergens adhering to fibers automatically under humidities normally used without newly applying allergen-suppression process and a method of producing the same.

BACKGROUND ART

In recent years, many allergic diseases such as atopic dermatitis, bronchial asthma, and allergic rhinitis have become a problem. The main reason for these allergic diseases is that many allergens such as allergens of house mites (Der1, Der2), particularly dust mites which are present in plenty in house dust, and allergens of Japanese cedar pollens (Crij1, Crij2) which are mainly raging in spring increase in a life space.

Particularly as for the allergens of dust mites, even if dust mites causing the allergens are destroyed, these dead mites supply furthermore allergic substances to a life space, and therefore it was difficult to resolve fundamentally allergic diseases resulting from the allergens of dust mites.

And, Crij1 which is an allergen of Japanese cedar pollens is glycoprotein having a molecular weight of about 40 kDa and Crij2 is glycoprotein having a molecular weight of about 37 kDa, and they are discerned as a xenobiotics to cause inflammation reaction when they adhere to nasal mucosa.

These allergens are apt to accumulate in decorative house materials such as a straw tatami mat, a floor (flooring) and a wallcovering, or bedclothes such a futon, a pillow, a blanket, a mattress, a bed mat and a sheet, and covers thereof; furniture made of cloth such as a sofa, a chair and a bed, which are made of cloth, and covers of furniture; filters of an air cleaner, an air conditioner and a vacuum cleaner; automobile implements such as a car sheet, a car mat and a child seat; toys such as a stuffed toy; and between fibers of fiber products such as a carpet, a curtain, clothes and a towel.

Particularly, because when patients suffering from allergic diseases are in contact with bedclothes in which allergens are accumulated for long time, their sleeps are interfered and their health is further damaged significantly at the occurrence of allergic symptoms, it is most desired to patients suffering from allergic diseases to suppress allergens.

In order to mitigate the symptoms of allergic diseases or prevent new sensitization, it is necessary to eliminate the allergens completely from a life space or to inactivate the allergens by modifying the allergens or the like.

As a method of eliminating the allergens from a life space among these countermeasures, a method of controlling the grain of a cloth of bedclothes cover to a certain size is disclosed in Japanese Kokai Publication Sho-62-213707 and a technology of preventing mites from penetrating into a futon by controlling a fixation method of futon's inner cotton in a cloth is disclosed in Japanese Kokoku Publication Hei-7-32735, and its products are actually commercialized. However, in these bedclothes, though the mites cannot pass through the bedclothes, a sufficient effect of suppressing an allergen could not be attained because sizes of the corpses and the egesta of mites which become allergens are one-tenth of that of mites or smaller and these allergens are pulverized by physical impact and become fine, and the penetration of these allergens cannot be protected. Much less, these bedclothes did not exert any effect on allergens not in bedclothes but in dust coming on from indoor and outdoor.

On the other hand, various methods of inactivating allergens are explored such that a method of using tannic acid as an inactivating agent for allergens is disclosed in Japanese Kokai Publication Sho-61-44821, but most of conventional methods of inactivating allergens are a method of inactivating allergens in an aqueous solution, for example, spraying a component suppressing an allergen. However, these methods were not only burdensome but also hard to process uniformly and had a problem that an area contaminated by allergens always adversely affects the human body before processing further.

Further, in Japanese Kokai Publication 2002-326944, a formulation which inactivates allergens in the air by including a hygroscopic composition such as alkaline earth salts in an allergen inactivating agent is disclosed, but there was a problem that when bedclothes were processed with this formulation, bedclothes became sticky because of the deliquescence of alkaline earth salt and the feeling of bedclothes was not adequate so that the formulation could not be used.

SUMMARY OF THE INVENTION

In view of the above-mentioned state of the art, the present invention aims to provide an allergen suppressor exerting an effect of suppressing an allergen under humidities normally used, and an allergen-suppression processed fiber, which can suppress an allergen adhering to fibers automatically without applying an allergen-suppression process and a method of producing the same.

An allergen suppressor of the present invention contains a hydrophilic polymer and a component suppressing an allergen. The above-mentioned hydrophilic polymer preferably has a melting point of 40° C. or higher. And, the above-mentioned hydrophilic polymer preferably satisfies the following conditions (1) and/or (2):

condition (1): a hydrophilic polymer has an ether bond and/or an amide bond in a main chain; and condition (2): a hydrophilic polymer has at least one polar group selected from the group consisting of an amine group, an ammonium salt group, a carboxyl group, a sulfone group, an ester group, a hydroxyl group and an amide group on a side chain.

The above-mentioned hydrophilic polymer is preferably at least one selected from the group consisting of a polysaccharide, an alcoholic resin, an acrylic resin, an ether resin, an amide resin and a urethane resin.

The above-mentioned hydrophilic polymer is more preferably at least one selected from the group consisting of a polyether, a polyvinyl alcohol, a polyacrylic acid, a polyacrylate salt, a polyacrylamide and a polyvinylpyrrolidone.

Further, preferably, at least two species of the hydrophilic polymers having different structures are used in combination.

In the allergen suppressor of the present invention, it is preferred that the hydrophilic polymer is mixed in proportions of 40 to 1000 weight % with respect to 100 weight % of the component suppressing an allergen.

An allergen-suppression processed fiber of the present invention is processed with the allergen suppressor of the present invention.

The allergen-suppression processed fiber of the present invention is produced by a method comprising the steps of processing fibers with the allergen suppressor of the present invention and the step of insolubilizing the hydrophilic polymer.

DETAILED DESCRIPTION OF THE INVENTION

Hereinafter, the present invention will be described in detail.

The allergen suppressor and the allergen-suppression processed fiber of the present invention have an effect of suppressing an allergen.

In the present description, an effect of suppressing an allergen refers to an effect of modifying or adsorbing allergens such as allergens of dust mites (Der1, Der2), allergens of Japanese cedar pollens (Crij1, Crij2) floating in the air, and allergens resulting from dogs and cats (Can f1, Fel d1), and suppressing the reactivity to a specific antibody of the allergen.

Examples of techniques of identifying such an effect of suppressing an allergen include such as a technique of measuring an amount of allergens according to an ELISA method using, for example, an ELISA kit (for example, manufactured by LCD Allergy Research Institute).

And, it is not necessarily definite what is the level of suppressing an allergen from which it is considered to have sufficient effect of suppressing an allergen, but for example, the sanitary guideline on the surface of futon ("Indoor contamination and allergy" by Midori Yoshikawa et al., INOUE SHOIN CO., LTD., 1999) states that in the case of Der 1 which is the total of allergens resulting from the egesta of *dermatophagoides pteronyssinus* and *dermatophagoides farinae*, it is preferred that Der 1, which has adhered to the surface of a futon in an amount 2000 to 3000 $ng/m^2$, can be reduced to below 1000 $ng/m^2$.

The allergen suppressor of the present invention contains a hydrophilic polymer which can form a reaction field capable of causing an interaction with an allergen by collecting water molecules in the air, and a component suppressing an allergen. In the fiber processed such an allergen suppressor, it becomes possible to exert an effect of suppressing an allergen under normal room conditions, for example, in an atmosphere of not more than 50 $g/m^3$ in absolute humidity.

Accordingly, the allergen-suppression processed fiber of the present invention exerts an effect of suppressing an allergen without making the fiber highly wet artificially by spraying or the like.

The reaction field capable of causing an interaction with the allergen refers to a reaction field for exerting some chemical interaction in order to suppress the antigenicity of a site (epitope) where the allergen develops the antigenicity, and it refers to a reaction field where spontaneous proceeding of a chemical reaction can take place, for example, by stabilizing an electrochemical transition state such as an ionized state to lower the level of an energy barrier in a transition state of a chemical reaction.

Generally, in order to lower the level of an energy barrier in a transition state which have to be overcome for initiating a chemical reaction, water in liquid form is required, but in the allergen suppressor and the allergen-suppression processed fiber of the present invention, it is not necessary to carry out the operations of sprinkling water or the like because such a reaction field can be formed by collecting water in the air.

In the present invention, the hydrophilic polymer to be used as a compound collecting water molecules in the air does not exhibit a deliquescence property under normal room conditions. The hydrophilic polymer used in the present invention is preferably a hydrophilic polymer having a melting point of 40° C. or higher. When the melting point is lower than 40° C., the hydrophilic polymer may become liquid in an atmosphere of use and an allergen-suppression processed product may become sticky to impair its feeling. Further, when the hydrophilic polymer is applied to products often coming into contact with water through cleaning or the like in daily life of a fiber, a hydrophilic polymer having a melting point of 50° C. or higher is more preferred from the viewpoint of sustaining an effect of suppressing an allergen.

As the above-mentioned hydrophilic polymer, a polymer satisfying the following conditions (1) and/or (2) is preferred:

condition (1): the hydrophilic polymer has an ether bond and/or an amide bond in a main chain; and condition (2): the hydrophilic polymer has at least one polar group selected from the group consisting of a cationic group like an amine group such as a primary amine, a secondary amine or a tertiary amine, and an ammonium salt group; an anionic group like a carboxyl group, a sulfone group and an ester group such as a sulfate ester or phosphate ester; and a nonionic group like a hydroxyl group and an amide group on a side chain.

The hydrophilic polymer used in the present invention is not particularly limited as long as it satisfies the above-mentioned condition (1) and/or (2), and examples of the hydrophilic polymers include a polysaccharide, an alcoholic resin, an acrylic resin, an ether resin, an amide resin and a urethane resin, and specifically include a polysaccharide such as starch, cellulose, tannin, lignin, alginic acid and gum arabic in natural compounds, and a polyether like a poly(ethylene oxide) such as polyethylene glycol, and a poly(methylene oxide) such as polypropylene glycol; a polyalcohol such as polyvinyl alcohol and butyral; a polymer acid such as polyacrylic acid; a polymer salt such as sodium polyacrylate; a polyamine such as polyallylamine; a polyacrylamide, a polyvinylpyrrolidone, a polyurethane resin, an acrylic resin or the like in synthetic compounds. Among others, a polyether, a polyvinyl alcohol, a polyacrylic acid, a polyacrylate salt such as sodium polyacrylate, a polyacrylamide and a polyvinylpyrrolidone are suitable because they have not only high hygroscopicity but also a high water holding property. These hydrophilic polymers may be used alone or in combination of two or more species, but it is preferred that two or more species of the hydrophilic polymers having different structures are used in combination. Examples of the combinations of the hydrophilic polymers having different structures include a combination of polyether of polyethylene glycol and sodium polyacrylate, and polymer salt, and a combination of polyether of polyethylene glycol and polyvinyl alcohol, and polyalcohol.

An amount of the above-mentioned hydrophilic polymer to be mixed is preferably not less than 40 weight % and not more than 1000 weight % with respect to 100 weight % of the component suppressing an allergen. When this amount is less than 40 weight %, the hydrophilic polymer cannot adequately collect water molecules in the air, and therefore there may be cases where a sufficient reaction field to cause an interaction with an allergen cannot be formed and a sufficient effect of suppressing an allergen cannot be exerted. And, when this amount is more than 1000 weight %, the content of the component suppressing an allergen in the allergen suppressor becomes less and the allergen-suppression processed fiber or the like cannot sufficient exert an effect of suppressing an allergen. This amount is more preferably not less than 50 weight % and not more than 1000 weight %, and furthermore preferably not less than 50 weight % and not more than 500 weight %.

The allergen-suppression processed fiber of the present invention is processed with the allergen suppressor of the present invention. When a fiber is processed with the allergen suppressor of the present invention, an amount of the allergen suppressor with respect to an amount of the fiber ranges from 0.1 weight % of a lower limit to 300 weight % of an upper limit. When this amount is less than 0.1 weight %, there may be cases where an effect of suppressing an allergen cannot be attained, and when it is more than 300 weight %, the fiber may be damaged. More preferably, a lower limit is 0.2 weight % and an upper limit is 100 weight %, and furthermore preferably, a lower limit is 0.5 weight % and an upper limit is 50 weight %.

The above-mentioned fiber is not particularly limited but a fiber having hygroscopicity is preferred from the viewpoint of forming a reaction field capable of causing an interaction with an allergen by collecting water molecules in the air. As such a fiber having hygroscopicity, for example, a natural fiber such as wool, silk, hemp and cotton, and a reclaimed fiber such as cupra and rayon as well as a chemical fiber having a high moisture-absorbing power such as acetate and nylon can be employed. And, by employing a chemical fiber of which a surface configuration or a sectional shape are modified or a structure is made porous or a fiber of which the moisture-absorbing/releasing properties is improved by applying special processing such as copolymerizing, blending, forming into a core-and-sheath structure, or combining to the surface of a fiber polymer having moisture-absorbing/releasing properties, an amount of the hydrophilic polymer in the allergen suppressor can be reduced and the feeling of the allergen-suppression processed fiber is improved. Particularly, a cotton fiber is preferred in the viewpoint of having high hygroscopicity.

The above-mentioned fiber, which can form a reaction field capable of causing an interaction with an allergen by collecting water molecules in the air, preferably has the surface which is neutral or alkaline. Specifically, the surface of the fiber preferably has a pH of 6 or higher. When the surface of the fiber has a pH of 6 or higher, the effect of suppressing an allergen is furthermore improved.

In addition, a method of measuring a pH of the surface of the fiber includes, for example, a method in which pure water is added dropwise to the surface of the fiber and the fiber is left at rest for about 15 minutes until the surface becomes wet well and then a pH is measured with a pH test paper.

The above-mentioned component suppressing an allergen is not particularly limited as long as it is a component which inactivates an allergen by modifying the allergen or the like and can suppress an antigen-antibody reaction, and examples of the component suppressing an allergen include a botanical extract such as tannic acid and catechin, a hydroxybenzoic acid such as 2,6-dihydroxybenzoic acid, an aromatic hydroxyl compound, a carbonate salt of alkali metal, an alum, a laurylbenzene sulfonate salt, a lauryl sulfate salt, a polyethylene oxide lauryl ether sulfate salt, a phosphate salt, zinc sulfate and/or lead acetate or the like. The above-mentioned component suppressing an allergen is preferably a substance which is in a solid state at room temperature from the viewpoint of a feeling that a product produced with the allergen suppressor becomes sticky. And, when the above-mentioned component suppressing an allergen is applied to a product often coming into contact with water through cleaning or the like in daily life of a fiber, it is preferably a water-insoluble polymer compound from the viewpoint of sustaining an effect of suppressing an allergen.

Further, the allergen suppressor of the present invention may contain at least one of these components suppressing an allergen as an effective component, and it may contain the combination of two or more species.

The above-mentioned aromatic hydroxy compound is not particularly limited as long as it is a compound having an aromatic hydroxyl group and the effect of suppressing an allergen, and examples of the aromatic hydroxy compound include an aromatic hydroxy compound formed by polymerizing or copolymerizing a monomer containing at least one of substituents expressed by the following general formulas (1) to (6), an aromatic hydroxy compound having at least one substituent of substituents expressed by the following general formulas (1) to (6) in a linear polymer, an aromatic hydroxy compound formed by polymerizing or copolymerizing a monomer having an aromatic heterocyclic hydroxyl group, and an aromatic hydroxy compound having an aromatic heterocyclic hydroxyl group as a substituent in a linear polymer, and among others, the aromatic hydroxy compound having at least one substituent of substituents expressed by the following general formulas (1) to (6) in a linear polymer and the aromatic hydroxy compound having an aromatic heterocyclic hydroxyl group as a substituent in a linear polymer are preferred.

The aromatic hydroxy compound formed by polymerizing or copolymerizing a monomer containing at least one of substituents expressed by the following general formulas (1) to (6) will be described. The substituents of this aromatic hydroxy compound are expressed by the following general formulas (1) to (6).

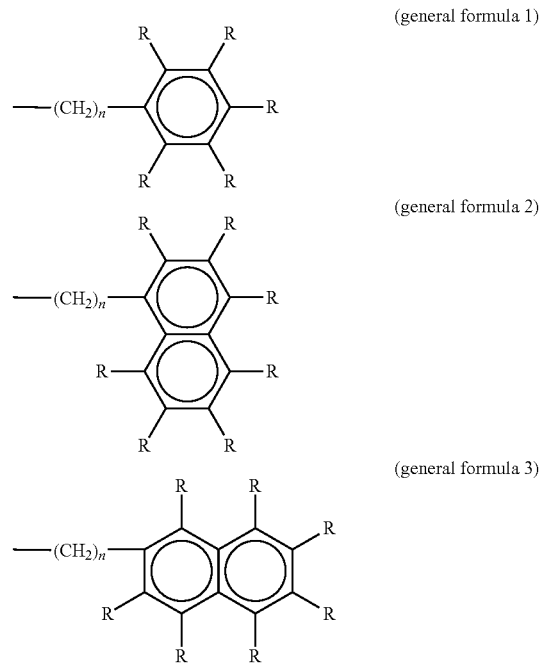

(general formula 4)

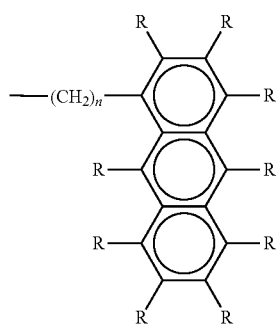

(general formula 5)

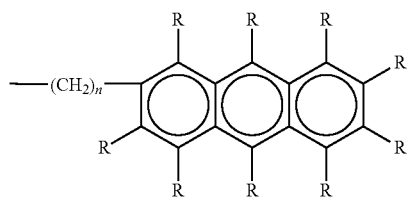

(general formula 6)

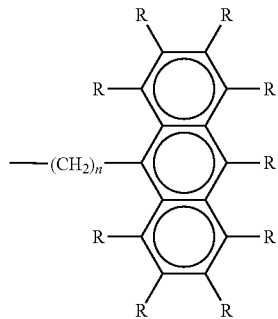

Further, in the above-mentioned general formulas (1) to (6), n is an integer of 0 to 5. The reason for this is that if n is 6 or more, the effect of suppressing an allergen, which substituents expressed by the above-mentioned general formulas (1) to (6) exhibit, becomes insufficient.

And, at least one of substituents R needs to be a hydroxyl group so that the aromatic hydroxy compound develops the effect of suppressing an allergen. However, the number of the hydroxyl groups is preferably one since a substance to which the allergen suppressor is applied becomes apt to color or discolor when the number of the hydroxyl groups is too much. That is, it is preferred that while only one of substituents R is a hydroxyl group, all substituents R other than this substituent are hydrogen.

Further, with respect to a position of the hydroxyl group, the hydroxyl group is preferably combined to the position where steric hindrance is lowest, and for example, in the case of the above-mentioned general formula (1), the hydroxyl group is preferably combined to a para-position.

The monomer containing at least one of substituents expressed by the above-mentioned general formulas (1) to (6) is not particularly limited as long as it has at least one of substituents expressed by the above-mentioned general formulas (1) to (6), and examples of the monomers include monomers having a monovalent phenolic group such as vinylphenol, tyrosine and 1,2-di(4-hydroxyphenyl)ethene (the following general formula (7)).

(general formula 7)

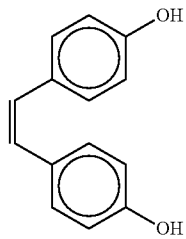

Further, a monomer capable of copolymerizing with the above-mentioned monomer containing at least one of substituents expressed by the above-mentioned general formulas (1) to (6), preferably having one or more monovalent phenolic group may be copolymerized with the above-mentioned monomer containing at least one of substituents expressed by the above-mentioned general formulas (1) to (6), preferably having one or more monovalent phenolic group to the extent of not impairing the suppressive effect on an allergen of an aromatic hydroxy compound.

Such a monomer includes, for example, ethylene, acrylate, methacrylate, methyl acrylate, methyl methacrylate, hydroxyethyl acrylate, hydroxyethyl methacrylate, hydroxypropyl acrylate, hydroxypropyl methacrylate, styrene or the like.

And, the linear polymer, to which each substituent expressed by the above-mentioned general formulas (1) to (6) is combined, is not particularly limited and includes a vinyl polymer, polyester, polyamide or the like. A chemical bond between this linear polymer and the substituent expressed by the above-mentioned general formulas (1) to (6) is not particularly limited and includes a carbon-to-carbon bond, an ester bond, an ether bond, an amide bond or the like.

Here, an aromatic hydroxy compound having at least one substituent of substituents expressed by the above-mentioned general formulas (1) to (6) in a linear polymer includes, for example, (a) a polymer or a copolymer of a monomer containing at least one of substituents expressed by the above-mentioned general formulas (1) to (6), and (b) a copolymer of a monomer containing at least one of substituents expressed by the above-mentioned general formulas (1) to (6) and a monomer which can copolymerize with this monomer or the like.

And, as the aromatic hydroxy compound having at least one substituent of substituents expressed by the above-mentioned general formulas (1) to (6) in a linear polymer, specifically, poly(vinyl 3,4,5-hydroxybenzoate), polyvinylphenol, polytyrosine, poly(1-vinyl-5-hydroxynaphthalene), poly(1-vinyl-6-hydroxynaphthalene) and poly(1-vinyl-5-hydroxyanthracene) are preferred.

In addition, a molecular weight of the aromatic hydroxy compound obtained by polymerizing the above-mentioned monomer is not particularly limited, but an aromatic hydroxy compound formed by polymerizing two or more monomers is preferred and an aromatic hydroxy compound formed by polymerizing five or more monomers is more preferred.

And, the above-mentioned aromatic heterocyclic hydroxy compound is not particularly limited as long as it performs a sufficient effect of suppressing an allergen, and examples of the compound include 2-hydroxyfuran, 2-hydroxythiophene, hydroxybenzofuran, 3-hydroxypyridine or the like.

Next, the aromatic hydroxy compound formed by polymerizing or copolymerizing a monomer having an aromatic heterocyclic hydroxyl group, such as the aromatic hydroxy compound having an aromatic heterocyclic hydroxyl group as a substituent in a linear polymer, will be described.

The above-mentioned aromatic heterocyclic hydroxyl group includes a group formed by combining a hydroxyl group to a heterocyclic skeleton such as thiophene and furan (the following general formulas (8), (9)), a group formed by combining a hydroxyl group to a skeleton having a heterocycle and an aromatic ring (the following general formula (10)), a group formed by combining a hydroxyl group and an alkyl group having 5 or less carbon atoms to a heterocyclic skeleton, and a group formed by combining a hydroxyl group and an alkyl group having 5 or less carbon atoms to a skeleton having a heterocycle and an aromatic ring.

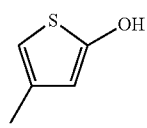

(general formula 8)

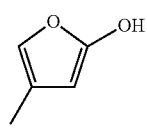

(general formula 9)

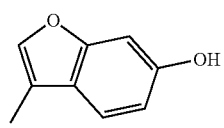

(general formula 10)

And, the linear polymer, to which an aromatic heterocyclic hydroxyl group is combined, is not particularly limited and includes a vinyl polymer, polyester, polyamide or the like. A chemical bond between this linear polymer and the aromatic heterocyclic hydroxyl group is not particularly limited and includes a carbon-to-carbon bond, an ester bond, an ether bond, an amide bond, or the like.

Such a compound formed by polymerizing or copolymerizing a monomer having an aromatic heterocyclic hydroxyl group includes, for example, (c) a polymer or a copolymer of a monomer having an aromatic heterocyclic hydroxyl group, (d) a copolymer of a monomer having an aromatic heterocyclic hydroxyl group and a monomer which can copolymerize with this monomer, or the like.

The above-mentioned monomer, which can copolymerize with a monomer having an aromatic heterocyclic hydroxyl group, includes, for example, ethylene, acrylate, methacrylate, methyl acrylate, methyl methacrylate, hydroxyethyl acrylate, hydroxyethyl methacrylate, hydroxypropyl acrylate, hydroxypropyl methacrylate, styrene, or the like.

The above-mentioned carbonate salt of alkali metal includes, for example, carbonate salts of alkali metals such as lithium, sodium, potassium, rubidium, cesium and francium. Among others, sodium carbonate and potassium carbonate are preferred.

The above-mentioned alum is highly safe because a part of the alum is designated as a food additive and a cosmetic material as potash alum and it is suitably used for a fiber or the like.

The above-mentioned alum includes, for example, double salt comprising aluminum sulfate and sulfate salt of a monovalent ion such as alkali metal, thallium and ammonium. Also, it includes double salt obtained by replacing the aluminum of the double salt with chromium, iron or the like.

Among others, aluminum potassium sulfate and aluminum sodium sulfate are suitable. The aluminum potassium sulfate which has particularly high capacity of suppressing an allergen is dodecahydrate ($AlK(SO_4)_2 \cdot 12H_2O$) or anhydride ($AlK(SO_4)_2$), but it may be partial hydrate existing in the process of losing a water molecule of the hydrate in stages.

The above-mentioned laurylbenzene sulfonate salt, lauryl sulfate salt, and polyethylene oxide lauryl ether sulfate salt include, for example, salt of metals such as lithium, sodium, potassium, magnesium or the like, and amine salts such as ammonium salt, triethanolamine or the like. Among others, sodium salt and triethanolamine are preferred.

The above-mentioned phosphate salt refers to salt which produces $PO_4^{3-}$ ion in dissolving in an aqueous solvent, and examples of the salt include sodium dihydrogenphosphate (sodium phosphate), disodium hydrogenphosphate (disodium phosphate), potassium dihydrogenphosphate or the like.

The above-mentioned zinc sulfate is heretofore known as zinc white or zinc flower and it is also listed in Japanese pharmaceutical codex. And, since the zinc sulfate is a food additive and is added to a breast milk substitution food for the purpose of supplying Zn which is a trace metal element essential to human growth and maintaining health, it is highly safe and suitably used for a fiber or the like.

As the above-mentioned zinc sulfate, hydrate (heptahydrate) or anhydride is mainly used, but the hydrate may be partial hydrate existing in the process of losing a water molecule of the hydrate in stages.

The above-mentioned lead acetate is heretofore known as sugar of lead and it is also listed in Japanese pharmaceutical codex.

As the above-mentioned lead acetate, hydrate (trihydrate) or anhydride is mainly used, but the hydrate may be partial hydrate existing in the process of losing a water molecule of the hydrate in stages.

In the allergen suppressor of the present invention, supplementary agents for formulations such as antioxidants and ultraviolet absorbers may be mixed to the extent of not impairing the effectiveness of effect of suppressing an allergen, and an acaricide, a disinfectant, a fungicide, or the like a deodorant may be contained in the allergen suppressor of the present invention.

A method of producing an allergen-suppression processed fiber of the present invention is not particularly limited but it preferably comprises the steps of processing fibers with the allergen suppressor of the present invention and the step of insolubilizing a hydrophilic polymer in water. A method of insolubilizing a hydrophilic polymer in water includes methods using a chemical reaction or crystallization. The above-mentioned chemical reaction includes, for example, a crosslinking reaction such as chemical crosslinking of crosslinking by using, for example, a crosslinking agent or the like, photo crosslinking of crosslinking by using a photo sensitizer and radiation crosslinking of crosslinking by radiation exposure, a graft polymerization reaction, and a reaction in which a hydrophilic side chain is converted to a hydrophobic side chain. As the above-mentioned method using crystallization, there is a method of crystallizing by heat treatment or by enhancing an intermolecular force by removing a substituent on a side chain. In addition, being insoluble in water preferably means that the solubility in 100 g of water is 10 g or less. When the solubility in 100 g of water is more than 10 g, the hydrophilic polymer runs off due to cleaning or the like in daily life and a sufficient reaction field capable of causing an interaction with an allergen cannot be formed, and therefore the effect of suppressing an allergen may become hard to show up. The solubility is more preferably 3 g or less, and furthermore preferably 1 g or less.

And, the above-mentioned component suppressing an allergen or hydrophilic polymer may be chemically combined with or post-fixed to the fiber.

Specifically, a method of doing so includes, for example, a method of chemically combining the component suppressing an allergen or the hydrophilic polymer with the fiber by a grafting reaction and a method of fixing the component suppressing an allergen or the hydrophilic polymer to the surface of the fiber by using a solvent and/or a binder.

When the above-mentioned grafting reaction is employed, a monomer, which is formed by adding reactivity or a polymerizing property to the above-mentioned component suppressing an allergen, can be used as a component suppressing an allergen, and among others, an aromatic hydroxy compound is suitable.

The above-mentioned grafting reaction is not particularly limited, and examples of the grafting reactions include a graft polymerization method in which a polymerization initiation point is made on a stem polymer to become fiber and on this point, a monomer forming a branch polymer which is a component suppressing an allergen or the like is polymerized; and a coupling method (a polymer reaction method) in which a branch polymer such as the component suppressing an allergen prepared in advance is combined to a stem polymer by a polymer reaction.

The above-mentioned graft polymerization is not particularly limited and examples of the graft polymerization methods include the following methods.

(1) A method in which a radical is produced by utilizing chain transfer reaction to a fiber and thereby polymerization is performed.

(2) A method in which an oxidation-reduction system (redox system) is formed by acting a reducing substance such as alcohol, thiol or amine on second-ceric salt, silver sulfate or the like and a free radical is produced in a fiber and thereby polymerization is performed.

(3) A method of irradiating a fiber and a monomer coexisting with a γ-ray or an accelerated electron beam, or a method of irradiating only a fiber and then adding a monomer to perform polymerization.

(4) A method in which a peroxy group is introduced by oxidizing a stem polymer or a diazo group is introduced from an amino group of a side chain and polymerization is performed by using the introduced group as a polymerization initiation point.

(5) A method of utilizing a polymerization initiation reaction of epoxy, lactam or polar vinyl monomer by an active group on a side chain such as a hydroxyl group, an amino group and a carboxyl group.

Examples of the above-mentioned graft polymerization methods include specifically the following methods: a) a method in which a free radical is produced by milling cellulose in a vinyl monomer to perform graft polymerization, b) a method in which graft polymerization is performed using a vinyl monomer and a cellulose derivative having a easy-to-transfer group as a fiber (for example, mercaptoethylcellulose or the like), c) a method in which a radical is produced by oxidizing ozone or peroxide and thereby graft polymerization is performed, d) a method of introducing a double bond such as allyl ether, vinyl ether or methacrylate ester into a side chain of cellulose to perform graft polymerization, e) a method in which sodium anthraquinone-2,7-disulfonate or the like is used as a photosensitizer and ultraviolet rays are irradiated and thereby graft polymerization is performed, f) a method in which fiber base materials are wound around a cathode and a monomer is added to dilute sulfuric acid and graft polymerization is electrochemically performed by applying an external voltage, g) a method of performing graft polymerization by heating a fiber to which glycidyl methacrylate (GMA) and benzoyl peroxide are applied in a monomer solution, and h) a method in which a monomer is added to a solution formed by dispersing benzoyl peroxide, a nonion-anionic surfactant and monochlorobenzene in water and in this mixture, for example, a polyester type fiber as a fiber are immersed and graft polymerization is performed by heating the resulting mixture.

Among others, considering that this graft polymerization is intended for a fiber, method g or h is suitable.

The above-mentioned coupling method is not particularly limited and examples of the coupling methods include (1) a chain transfer reaction, an oxidation reaction or a substitution reaction on C—H, (2) an addition reaction or an oxidation reaction on a double bond, (3) esterification, etherification or acetalization of a hydroxyl group, a substitution reaction, an addition reaction or a hydrolysis reaction on an ester group and an amide group, or a substitution reaction or a desorption reaction on a halogen group, and (4) a substitution reaction (halogenation, nitration, sulfonation, chloromethylation) on an aromatic ring.

The above-mentioned method of fixing the component suppressing an allergen or the hydrophilic polymer to the surface of a fiber by using a solvent and/or a binder includes a method of dissolving or dispersing the above-mentioned component suppressing an allergen or the like in a solvent and/or a binder and then chemically combining the dissolved or dispersed component suppressing an allergen or the like with the fiber and/or post-fixing it to the fiber. And, the method of chemically combining and/or post-fixing is not particularly limited and a method of coating the component suppressing an allergen may be used or a method of applying a solution containing the suppressive component onto the fiber by spraying may be used.

The above-mentioned solvent is not particularly limited as long as it is a substance which can dissolve or disperse the component suppressing an allergen or the hydrophilic polymer or a substance which can dissolve a binder, and examples of the solvents include water; alcohols such as methyl alcohol, ethyl alcohol and propyl alcohol; hydrocarbons such as toluene, xylene, methylnaphthalene, kerosene and cyclohexane; ethers such as diethyl ether, tetrahydrofuran and dioxane; ketones such as acetone and methyl ethyl ketone; and amides such as N,N-dimethylformamide.

The above-mentioned binder is not particularly limited as long as it is a substance which can fix the component suppressing an allergen or the hydrophilic polymer to the surface of a fiber, and examples of the binders comprising a synthetic resin include a one component urethane resin, a two component urethane resin, an acrylic resin, a urethane acrylate resin, a polyester resin, an unsaturated polyester resin, an alkyd resin, a vinyl acetate resin, a vinyl chloride resin, an epoxy resin, an epoxy acrylate resin or the like. Among others, urethane resins are preferred in the viewpoint of having hygroscopicity. When these binders are in a liquid state, they may be used as-is or may be used with the above-mentioned solvent added to the binder. When these binders are in a solid state, they may be used in a state of being dissolved or dispersed in the above-mentioned solvent. These solvents and binders may be used alone or in combination of two or more species.

The allergen-suppression processed fiber of the present invention can be also produced by spinning a fiber material, which is formed by copolymerization of a polymerizable monomer having the component suppressing an allergen or the hydrophilic polymer, into threads. Herein, the above-mentioned fiber material is formed by copolymerizing the polymerizable monomer having the component suppressing an allergen or the hydrophilic polymer with a polymerizable monomer to become a common fiber material.

The above-mentioned polymerizable monomer having the component suppressing an allergen or the hydrophilic polymer is not particularly limited as long as it is a monomer formed by providing a polymerizing property for the above-mentioned component suppressing an allergen or hydrophilic polymer.

And, the allergen-suppression processed fiber of the present invention can be also obtained by spinning the component suppressing an allergen and a fiber material into threads. As the fiber material referred to here, a fiber material formed by copolymerizing the polymerizable monomer having the component suppressing an allergen or the hydrophilic polymer with a polymerizable monomer to become a common fiber material and/or a common fiber material is used.

The above-mentioned common fiber material is not particularly limited as long as it is a raw material which is usually processed and used as fiber, and examples of the fiber materials include polyamide type fiber such as nylon; acrylic type fiber, polyvinylidene chloride, polyvinyl chloride, polyacrylonitrile and polyester; polyolefin type fibers such as polyethylene and polypropylene; and a synthetic fiber material such as polyurethane, a semisynthetic fiber material such as acetate, a reclaimed fiber material such as cupra and rayon, and a natural fiber.

Further, the allergen-suppression processed fiber of the present invention can also be produced by mixing the fiber material containing the above-mentioned component suppressing an allergen and the common fiber material together or twining these materials alternately, and then spinning.

A method of copolymerizing the above-mentioned component suppressing an allergen or hydrophilic polymer with the polymerizable monomer to become a fiber material is not particularly limited and include, and examples of the method include an addition reaction such as a vinyl polymerization, a cyclopolymerization and a ring-opening polymerization, a hydrogen migration polymerization such as a transition polymerization and an isomerizing polymerization, and a condensation reaction such as an oxidative polymerization, a denitrification polymerization, a decarboxylation polymerization, a polycondensation and an addition-condensation reaction.

The component suppressing an allergen or the hydrophilic polymer to be used for such a copolymerization reaction is not particularly limited as long as it is a monomer formed by providing a polymerizing property for the above-mentioned component suppressing an allergen or hydrophilic polymer, but among others, an aromatic hydroxy compound is suitable.

A method of spinning the above-mentioned component suppressing an allergen and the fiber material (a common fiber material, a fiber material containing a suppressive component) into threads is not particularly limited and includes the following methods.

(1) Melt spinning method: A method in which for example in a melt fiber material, after heating and melting the fiber material, a component suppressing an allergen, a decomposition point of which is above a heating-melting point of the fiber material, is blended into the melt fiber material to form a melt mixture, and this melt mixture is extruded into an inert cooling medium (for example, air, nitrogen, water or the like) through a spinneret having a desired fine bore and cooled/solidified to form a fiber.

(2) Wet spinning method: A method in which for example, the fiber material is dissolved in a solvent to prepare a solution, and in this, a component suppressing an allergen or the like is dispersed and mixed, or dissolved (spinning solution), and this solution is extruded into a liquid for reclaiming and coagulating a polymer through a spinneret to solidify a polymer melted in the spinning solution into the form of fiber.

(3) Dry spinning method: A method in which for example, the fiber material is dissolved in a volatile solvent, and in this, a component suppressing an allergen or the like is dispersed and mixed, or dissolved to form a spinning solution, and this solution is extruded into a heated vapor through a spinneret and the solvent in the spinning solution is vaporized to solidify a polymer into the form of fiber.

These three methods are industrially in widespread use and can be selectively employed in accordance with a desired allergen-suppression processed fiber.

Further, a method of spinning the component suppressing an allergen and the fiber material into threads other than the above-mentioned methods includes the following methods:

(4) Emulsion spinning method: A method in which an emulsion of the fiber material (suspension, slurry) is prepared, and in this, a component suppressing an allergen or the like is dispersed and mixed, or dissolved to form a spinning solution, and this solution is spun into threads according to the wet spinning method or the dry spinning method.

(5) Conjugate spinning method: A component suppressing an allergen or the like is dispersed and mixed, or dissolved in two or more components of melt substances of fiber material which have been melted separately, respectively, to form two or more components of melt substances, or the component suppressing an allergen or the like itself is melted to form a melt substance, and these melt substances are combined into one just before a spinneret and simultaneously spun into threads.

(6) Method of forming polymer material in fiber form without using a spinneret: A method in which for example, a thin film containing a component suppressing an allergen or the like is drawn, and then this thin film is cut thinly in the longitudinal direction and further drawn and subjected to heat setting, and a method of highly drawing a rod-like polymer material containing a component suppressing an allergen or the like.

(7) Method by interfacial polymerization.

The allergen-suppression processed fiber of the present invention can recover a function of suppressing an allergen by various techniques even after its suppressive effect on an allergen decreases once.

The above-mentioned recovering a function of suppressing an allergen means that when the allergen-suppression processed fiber has lost a function of suppressing an allergen due to repeated contact with allergens, it is brought into a state of being able to exert the function of suppressing an allergen again.

As for the inactivation of an allergen, it is thought that there are two cases where a suppressive component is consumed by a reaction between an allergen and a suppressive component resulting from the species of a suppressive component to be used and where a suppressive component catalytically inactivates an allergen. Accordingly, as a method of recovering a function of the suppressive component, for example, a method of exposing a new component suppressing an allergen at the surface of a fiber by exuding the suppressive component existing within a fiber to the surface or a method of eliminating an inactivated allergen deposited on the surface of a suppressive fiber is conceivable.

Specifically, a method of recovering the function of suppressing an allergen, which the allergen-suppression processed fiber of the present invention has, includes, for example, a method of cleaning the allergen-suppression processed fiber of the present invention with a liquid, a method of heating it, a method of draw it with a vacuum cleaner, or the like.

The above-mentioned liquid which can be used for cleaning is not particularly limited as long as it is not a substance damaging the fiber itself, and examples of the liquid include water; alcohols such as methyl alcohol, ethyl alcohol and propyl alcohol; hydrocarbons such as toluene, xylene, methylnaphthalene, kerosene and cyclohexane; ethers such as diethyl ether, tetrahydrofuran and dioxane; ketones such as acetone and methyl ethyl ketone; and amides such as N,N-dimethylformamide, or the like. Among others, water or alcohols are suitable because it is possible to process simply and easily in households. And, a surfactant commonly used may be used simultaneously in order to enhance a cleaning effect.

In the case of heating the allergen-suppression processed fiber of the present invention, a temperature to which the fiber is heated is not particularly limited as long as it does not damage the fiber itself, and further, a method of heating described above-mentioned is not particularly limited and includes, for example, a method of directly heating, a method of cleaning under heating the above-mentioned liquid, and a method of heating with sunlight.

Examples of an allergen for which the allergen suppressor and the allergen-suppression processed fiber of the present invention are intended include an animalistic allergen and a botanical allergen such as a pollen. An animalistic allergen on which the allergen suppressor and the allergen-suppression processed fiber of the present invention particularly have effects is an allergen of mite. The above-mentioned mite are living things of arthropoda-arachnida-acarina and classified into seven suborders, and include notostigmata typified by opilioacaridae, tetrastigmata typified by holothyridae, metastigmata typified by *ixodes ovatus* and Ixodidae, mesostigmata typified by *ornithonyssus bacoti* and *dermanyssus hirundinis*, prostigmata typified by *cheyletus malaccensis* and *tarsonemus granarius*, astigmata typified by *tyrophagus putrescentiae* and *dermatophagoides farinae*, and cryptostigmata typified by *haplochthonius simplex* and *cosmochthonius reticulatus*. The allergen suppressor and the allergen-suppression processed fiber of the present invention can be aimed at any of the above-mentioned mites but they have effects particularly on pyroglyphidae which are present in plenty in house dust, particularly in bedclothes, and causes allergic diseases.

The allergen-suppression processed fiber of the present invention can be suitably used for a fiber product like a bedclothe such a futon, a pillow, a blanket, a mattress, a bed mat and a sheet, and covers thereof; furniture made of cloth such as a sofa, a chair and a bed, which are made of cloth, and a cover of furniture; a filter of an air cleaner, an air conditioner and a vacuum cleaner; an automobile implement such as a car sheet, a car mat and a child seat; a toy such as a stuffed toy; and a carpet, a curtain, clothes and a towel.

An object and a location for which the allergen suppressor of the present invention is used are not particularly limited and include decorative house materials such as a straw tatami mat, a floor (flooring) and a wallcovering and a car's decorative material other than the above-mentioned applications. By processing these fiber products and various materials with the allergen suppressor of the present invention, it becomes possible to reduce the amount of allergens in all life environments. And, when the allergen suppressor of the present invention is processed by insolubilizing technology, the suppressive effect on an allergen is not deteriorated and can be exerted persistently even though water is spilled thereon or wiped out.

BEST MODE FOR CARRYING OUT THE INVENTION

Hereinafter, the present invention will be described in more detail by way of examples, but the present invention is not limited to these examples.

Example 1

An allergen suppressor was prepared using 18 parts by weight of polyvinylpyrrolidone K25 (produced by Wako Pure Chemical Industries, Ltd., Mw 35000), 12 parts by weight of KAYAHARD NHN (produced by Nippon Kayaku Co., Ltd., hydroxyl equivalent 139 to 147) and 100 parts by weight of ethanol. The obtained allergen suppressor was uniformly applied onto a polyester nonwoven fabric (grammage 100 g/m$^2$) by spraying in such a way that an applied rate was 20 µl/cm$^2$ and left standing at room temperature for 8 hours to dry to obtain a cloth made of allergen-suppression processed fibers.

Example 2

An allergen suppressor was prepared using 12 parts by weight of polyvinylpyrrolidone K25 (produced by Wako Pure Chemical Industries, Ltd., Mw 35000), 18 parts by weight of a phenolic resin "SUMILITERESIN" (PR-217 produced by SUMITOMO BAKELITE Co., Ltd.) and 100 parts by weight of DMF. The obtained allergen suppressor was uniformly applied onto a polyester nonwoven fabric (grammage 100 g/m$^2$) by spraying in such a way that an applied rate was 20 µl/cm$^2$ and left standing at 50° C. for 15 hours in an atmosphere of air circulation to dry to obtain a cloth made of allergen-suppression processed fibers.

Example 3

An allergen suppressor was prepared using 8 parts by weight of polyvinylpyrrolidone K30 (produced by Wako Pure Chemical Industries, Ltd., Mw 40000), 20 parts by weight of a phenolic resin "MILEX" (XLC-4L produced by Mitsui Chemicals, Inc.) and 100 parts by weight of DMF. The obtained allergen suppressor was uniformly applied onto a cotton-polyester mixture (8:2) nonwoven fabric (grammage 100 g/m$^2$) by spraying in such a way that an applied rate was 20 µl/cm$^2$ and left standing at 50° C. for 15 hours in an atmosphere of air circulation to dry to obtain a cloth made of allergen-suppression processed fibers.

Example 4

An allergen suppressor was prepared using 40 parts by weight of a 50 weight % aqueous solution of polyacrylamide (produced by Aldrich Chemical Co., Mw 10000), 10 parts by weight of polytyrosine (produced by ICN BIOCHEMICALS INC.: weight-average molecular weight Mw=18000 to 36000) and 80 parts by weight of purified water. The obtained allergen suppressor was uniformly applied onto a polyester nonwoven fabric (grammage 100 g/m$^2$) by spraying in such a way that an applied rate was 20 µl/cm$^2$ and left standing at room temperature for 8 hours to dry to obtain a cloth made of allergen-suppression processed fibers.

Example 5

An allergen suppressor was prepared using 15 parts by weight of sodium polyacrylate (produced by Aldrich Chemical Co., Mw 2100), 15 parts by weight of polyacrylic acid (produced by Wako Pure Chemical Industries, Ltd.), 12 parts by weight of KAYAHARD NHN (produced by Nippon Kayaku Co., Ltd., hydroxyl equivalent 139 to 147), 1 part by weight of EMAL 2F Needle (produced by Kao Corporation, solid content 90%) and 100 parts by weight of a 50 weight % aqueous solution of ethanol. The obtained allergen suppressor was uniformly applied onto a cotton cloth (grammage 100 g/m$^2$) by spraying in such a way that an applied rate was 20 μl/cm$^2$ and left standing at room temperature for 8 hours to dry to obtain a cloth made of allergen-suppression processed fibers.

Example 6

An allergen suppressor was prepared using 1 part by weight of polyethylene glycol (produced by Wako Pure Chemical Industries, Ltd.: Mw 7500), 5 parts by weight of sodium polyacrylate (produced by Aldrich Chemical Co., Mw 2100), 10 parts by weight of poly-p-vinylphenol "MARUKA LYNCUR M" (produced by Maruzen Petrochemical Co., Ltd., weight-average molecular weight Mw=5500), 1 part by weight of EMAL 2F Needle (produced by Kao Corporation, solid content 90%) and 100 parts by weight of a 50 weight % aqueous solution of ethanol. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

Example 7

An allergen suppressor was prepared using 3 parts by weight of polyethylene glycol (produced by Wako Pure Chemical Industries, Ltd.: Mw 7500), 3 parts by weight of polyvinyl alcohol (produced by Aldrich Chemical Co., Mw 2100), 12 parts by weight of poly-p-vinylphenol "MARUKA LYNCUR M" (produced by Maruzen Petrochemical Co., Ltd., weight-average molecular weight Mw=5500), 1 part by weight of EMAL 2F Needle (produced by Kao Corporation, solid content 90%) and 100 parts by weight of a 50 weight % aqueous solution of ethanol. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

Example 8

An allergen suppressor was prepared using 40 parts by weight of a 50 weight % aqueous solution of polyacrylamide (produced by Aldrich Chemical Co., Mw 10000), 10 parts by weight of polytyrosine (produced by ICN BIOCHEMICALS INC., weight-average molecular weight Mw=18000 to 36000) and 80 parts by weight of purified water. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry, and then the dried allergen suppressor was heated at 100° C. for 30 minutes, at 120° C. for 30 minutes, at 150° C. for 1 hour and at 170° C. for 30 minutes in an atmosphere of nitrogen to obtain a cloth made of allergen-suppression processed fibers.

Example 9

20 parts by weight of polyvinyl alcohol 3500 (produced by Wako Pure Chemical Industries, Ltd., saponification degree 86 to 90 mol %), 20 parts by weight of poly-p-vinylphenol "MARUKA LYNCUR M" (produced by Maruzen Petrochemical Co., Ltd., weight-average molecular weight Mw=5500), 2 parts by weight of a copolymer of ethyl acrylate and methyl methacrylate "Eudragit NE 30D" (produced by Rohm Pharma: solid content 30%) as a binder, 0.3 parts by weight of a nonionic surfactant "EMULGEN 911" (produced by Kao Corporation), 100 parts by weight of purified water as a solvent, and 0.1 parts by weight of barium hydroxide (produced by Wako Pure Chemical Industries, Ltd.) for making the surface of fibers alkaline were mixed and stirred to prepare an allergen suppressor. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

Example 10

An allergen suppressor was prepared by adding 100 parts by weight of 4-vinylphenol (produced by Lancaster Synthesis Ltd.: purity in a propylene glycol solution is 10%) and 40 parts by weight of polyethylene glycol (produced by Wako Pure Chemical Industries, Ltd.: Mw 7500) to an aqueous emulsified dispersion comprising 1 part by weight of benzoyl peroxide (produced by Sigma-Aldrich Co.: purity 75% first class grade), 1 part by weight of EMAL 2F Needle (produced by Kao Corporation: effective component or solid content 90%), 10 parts by weight of chlorobenzene (produced by Sigma-Aldrich Co.: purity 99.5% analytical grade) and 1000 parts by weight of purified water.

A polyethylene terephthalate (PET) cloth of 10 cm×10 cm was immersed in the allergen suppressor and graft polymerization was performed by heating at 100° C. for 60 minutes. After this, the processed PET cloth was extracted for 30 minutes in purified water of 100° C. and further neutralized at 50° C. for 30 minutes with a 0.5% aqueous solution of sodium hydroxide in order to make the surface of fibers neutral, and then the PET cloth was washed with water and dried to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 7.0.

Example 11

100 parts by weight of polyethylene terephthalate (limiting viscosity number [η]=0.65), 20 parts by weight of poly-p-vinylphenol "MARUKA LYNCUR M" (produced by Maruzen Petrochemical Co., Ltd., weight-average molecular weight Mw=5500) and 30 parts by weight of moisture permeable polyurethane (Erastollan produced by TAKEDA-BADISCH URETHANE INDUSTRIES LTD.) were kneaded at 260° C. for 20 minutes. After kneading, a mixture was extruded with a screw type uniaxial extruder and molded in pellet form.

The obtained pellet was spun into threads by melt spinning method (A pack filter in spinning has 270 mesh), drawn, washed with water and dried to obtain allergen-suppression processed fibers. Further, these fibers were made in a plain weave to obtain a cloth made of allergen-suppression processed fibers.

Example 12

The same procedure as in Example 7 was performed except for using polyethylene glycol having a molecular weight of 400 in place of polyethylene glycol having a molecular weight of 7500.

Example 13

The same procedure as in Example 1 was performed except for adding 3 parts by weight of polyvinylpyrrolidone K25 (produced by Wako Pure Chemical Industries, Ltd., Mw 35000) in place of adding 18 parts by weight thereof.

Example 14

An allergen suppressor was prepared using 6 parts by weight of polyethylene glycol (produced by Wako Pure Chemical Industries, Ltd.: Mw 7500), 15 parts by weight of tannic acid (produced by Tokyo Chemical Industry CO., LTD.) and 100 parts by weight of ethanol. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

Example 15

An allergen suppressor was prepared using 6 parts by weight of polyethylene glycol (produced by Wako Pure Chemical Industries, Ltd.: Mw 7500), 20 parts by weight of sodium lauryl sulfate (produced by Wako Pure Chemical Industries, Ltd.), 1 part by weight of EMAL 2F Needle (produced by Kao Corporation, solid content 90%) and 100 parts by weight of a 50 weight % aqueous solution of ethanol. The allergen suppressor was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

Example 16

A fiber treatment solution was prepared by adding 100 parts by weight of 4-vinylphenol (produced by Lancaster Synthesis Ltd.: purity in a propylene glycol solution is 10%) and 20 parts by weight of polyethylene glycol (produced by Wako Pure Chemical Industries, Ltd.: Mw 7500) as a hydrophilic polymer to an aqueous emulsified dispersion comprising 1 part by weight of benzoyl peroxide (produced by Sigma-Aldrich Co.: purity 75% first class grade), 1 part by weight of "EMAL 2F Needle" (produced by Kao Corporation: effective component or solid content 90%), 10 parts by weight of chlorobenzene (produced by Sigma-Aldrich Co.: purity 99.5% analytical grade) and 1000 parts by weight of purified water.

20 parts by weight of a polyethylene terephthalate (PET) cloth was immersed in the fiber treatment solution and graft polymerization was performed by heating at 100° C. for 60 minutes. After this, the processed PET cloth was extracted for 30 minutes in purified water of 100° C. and further neutralized at 50° C. for 30 minutes with a 0.5% aqueous solution of sodium hydroxide in order to make the surface of a fiber neutral, and then the PET cloth was washed with water and dried to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 7.0.

Example 17

2 parts by weight of polytyrosine (produced by ICN BIO-CHEMICALS INC.: weight-average molecular weight Mw=18000 to 36000), 2 parts by weight of polyethylene glycol (produced by Wako Pure Chemical Industries, Ltd.: Mw 7500), 2 parts by weight of a copolymer of ethyl acrylate and methyl methacrylate "Eudragit NE 30D" (produced by Rohm Pharma: solid content 30%) as a binder, 0.3 parts by weight of a nonionic surfactant "EMULGEN 911" (produced by Kao Corporation), 100 parts by weight of purified water as a solvent, and 0.1 parts by weight of barium hydroxide (produced by Wako Pure Chemical Industries, Ltd.) for making the surface of a fiber alkaline were mixed and stirred to prepare a fiber treatment solution. The fiber treatment solution was uniformly applied onto a polyester nonwoven fabric (grammage 100 g/m$^2$) by spraying in such a way that an applied rate was 20 μl/cm$^2$ and left standing at room temperature for 8 hours to dry to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 8.3.

Example 18

100 parts by weight of polyethylene terephthalate (limiting viscosity number [η]=0.65), 20 parts by weight of poly-p-vinylphenol "MARUKA LYNCUR M" (produced by Maruzen Petrochemical Co., Ltd., weight-average molecular weight Mw=5500), 10 parts by weight of polypropylene glycol (diol type, produced by Wako Pure Chemical Industries, Ltd.: average molecular weight 3000) and 10 parts by weight of magnesium hydroxide (produced by Wako Pure Chemical Industries, Ltd.) were kneaded at 260° C. for 20 minutes with a pressure kneader. After kneading, a mixture was extruded with a screw type uniaxial extruder and molded in pellet form.

The obtained pellet was spun into threads by melt spinning (A pack filter in spinning has 270 mesh), drawn, washed with water and dried to obtain allergen-suppression processed fibers. Further, these fibers were made in a plain weave to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 11.0.

Example 19

A fiber treatment solution was prepared by adding 100 parts by weight of 4-vinylphenol (produced by Lancaster Synthesis Ltd.: purity in a propylene glycol solution is 10%) and 20 parts by weight of polyethylene glycol (produced by Wako Pure Chemical Industries, Ltd.: Mw 7500) as a hydrophilic polymer to an aqueous emulsified dispersion comprising 1 part by weight of benzoyl peroxide (produced by Sigma-Aldrich Co.: purity 75% first class grade), 1 part by weight of "EMAL 2F Needle" (produced by Kao Corporation: effective component or solid content 90%), 10 parts by weight of chlorobenzene (produced by Sigma-Aldrich Co.: purity 99.5% analytical grade) and 1000 parts by weight of purified water.

20 parts by weight of a polyethylene terephthalate (PET) cloth was immersed in the fiber treatment solution obtained and graft polymerization was performed by heating at 100° C. for 60 minutes. After this, the processed PET cloth was extracted for 30 minutes in purified water of 100° C. and further processed at 50° C. for 30 minutes with 0.1N hydrochloric acid in order to make the surface of a fiber acidic, and then the PET cloth was washed with water and dried to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 3.0.

Example 20

2 parts by weight of polytyrosine (produced by ICN BIOCHEMICALS INC.: weight-average molecular weight Mw=18000 to 36000), 2 parts by weight of polyethylene glycol (produced by Wako Pure Chemical Industries, Ltd.: Mw 7500), 2 parts by weight of a copolymer of ethyl acrylate and methyl methacrylate "Eudragit NE 30D" (produced by Rohm Pharma: solid content 30%) as a binder, 0.3 parts by weight of a nonionic surfactant "EMULGEN 911" (produced by Kao Corporation), 100 parts by weight of purified water as a solvent, and 0.1 parts by weight of 0.01N sulfuric acid (produced by Wako Pure Chemical Industries, Ltd.) for making the surface of a fiber acidic were mixed and stirred to prepare a fiber treatment solution.

The obtained fiber treatment solution was uniformly applied onto a polyester nonwoven fabric (grammage 100 g/m$^2$) by spraying in such a way that an applied rate was 20 µl/cm$^2$ and left standing at room temperature for 8 hours to dry to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 3.3.

Example 21

100 parts by weight of polyethylene terephthalate (limiting viscosity number [η]=0.65), 20 parts by weight of poly-p-vinylphenol "MARUKA LYNCUR M" (produced by Maruzen Petrochemical Co., Ltd., weight-average molecular weight Mw=5500), 10 parts by weight of polypropylene glycol (diol type, produced by Wako Pure Chemical Industries, Ltd.: average molecular weight 3000) and 1 part by weight of iron (III) chloride (produced by Wako Pure Chemical Industries, Ltd.) were kneaded at 260° C. for 20 minutes with a pressure kneader. After kneading, a mixture was extruded with a screw type uniaxial extruder and molded in pellet form.

The obtained pellet was spun into threads by melt spinning (A pack filter in spinning has 270 mesh), drawn, washed with water and dried to obtain allergen-suppression processed fibers. Further, these fibers were made in a plain weave to obtain a cloth made of allergen-suppression processed fibers.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 2.7.

Comparative Example 1

The PET cloth used in Example 1 was used without processing with an allergen suppressor.

Comparative Example 2

The same procedure as in Example 1 was performed except for not using KAYAHARD NHN.

Comparative Example 3

The same procedure as in Example 4 was performed except for not using polytyrosine.

Comparative Example 4

The same procedure as in Example 5 was performed except for not using KAYAHARD NHN.

Comparative Example 5

The same procedure as in Example 6 was performed except for not using poly-p-vinylphenol "MARUKA LYNCUR M".

Comparative Example 6

The same procedure as in Example 9 was performed except for not using poly-p-vinylphenol "MARUKA LYNCUR M".

Comparative Example 7

The same procedure as in Example 10 was performed except for not using poly-p-vinylphenol "MARUKA LYNCUR M".

Comparative Example 8

The same procedure as in Example 1 was performed except for not using 18 parts by weight of polyvinylpyrrolidone K25 (produced by Wako Pure Chemical Industries, Ltd., Mw 35000).

Comparative Example 9

The same procedure as in Example 2 was performed except for not using 12 parts by weight of polyvinylpyrrolidone K25 (produced by Wako Pure Chemical Industries, Ltd., Mw 35000).

Comparative Example 10

The same procedure as in Example 3 was performed except for not using 8 parts by weight of polyvinylpyrrolidone K30 (produced by Wako Pure Chemical Industries, Ltd., Mw 40000).

Comparative Example 11

The same procedure as in Example 4 was performed except for not using 40 parts by weight of a 50 weight % aqueous solution of polyacrylamide (produced by Aldrich Chemical Co., Mw 10000).

Comparative Example 12

The same procedure as in Example 4 was performed except for using 20 parts by weight of calcium chloride dehydrate in place of 40 parts by weight of a 50 weight % aqueous solution of polyacrylamide (produced by Aldrich Chemical Co., Mw 10000).

Comparative Example 13

The same procedure as in Example 11 was performed except for not using 20 parts by weight of poly-p-vinylphenol "MARUKA LYNCUR M" (produced by Maruzen Petrochemical Co., Ltd., weight-average molecular weight Mw=5500)

Comparative Example 14

The same procedure as in Example 7 was performed except for not using polyethylene glycol and polyvinyl alcohol.

Comparative Example 15

The PET cloth used in Example 16 was used without processing with an allergen suppressor to obtain a cloth.

Comparative Example 16

Polyethylene terephthalate (limiting viscosity number [η]0.65) was extruded with a screw type uniaxial extruder and molded in pellet form. The obtained pellet was spun into threads by the same method as in Example 18 (A pack filter in spinning has 270 mesh), drawn, washed with water and dried to obtain fibers. Further, these fibers were made in a plain weave to obtain a cloth.

In addition, a pH of the surface of the obtained cloth was measured by a method in which pure water was added dropwise to the surface of the obtained cloth and the cloth was left at rest for 15 minutes until the surface became wet well and then a pH was measured with a pH test paper, and consequently it was pH 6.7.

(Evaluation of Suppressive Effect on Allergen)

Using the cloths prepared in Examples 1 to 21 and Comparative Examples 1 to 17, five cloth pieces for evaluation having a size of 10 cm×10 cm were prepared for each cloth. On this cloth piece for evaluation, 5 mL of a prepared allergen solution, which is formed by dispersing 1 part by weight of dust and dirt (containing Der p1 allergen in an amount 10 μg per 1 g) in a solution comprising 90 parts by weight of ethyl alcohol and 10 parts by weight of purified water, was sprinkled, and the cloth piece for evaluation was dried for 5 minutes in an oven of 50° C. to prepare a sample for evaluation.

On this sample, an amount of an allergen was measured immediately after drying and after leaving standing for 15 hours in a thermo-hygrostat of 25° C. and 60% in RH according to the following method, and an allergen suppression rate was determined from the equation (I).

Allergen suppression rate (%)=(1−amount of allergen after leaving standing at 25° C. and 60% in RH for 15 hours/amount of allergen immediately after drying)×100   (I)

First, the cloth piece for evaluation, in which the allergen was included, was rolled and put in a 15 mL glass test tube, and to this, 10 mL of an extracting solution (formed by adding 1 weight % of BSA and 0.05 weight % of Tween 20 to a phosphate buffer (pH 7.35)) was added, and the resulting mixture was shaken well for 20 minutes and immediately, the extracting solution was sampled.

An amount of an allergen in the obtained extracting solution was measured using an ELISA kit (manufactured by LCD Allergy Research Institute) and converted to an amount of Der p1 per 1 $m^2$.

(Evaluation of Feeling)

After each of the cloths prepared in Examples 1 to 15 and Comparative Examples 1 to 14 was left standing for 15 hours in a thermo-hygrostat of 38° C. and 75% in RH, a sticky feeling thereof was evaluated. The cloth on which the sticky feeling was not perceived in touching the cloth with fingers was rated as 4, and the cloth on which the sticky feeling was perceived a little was rated as 3, and the cloth on which there was not problems in using the cloth but the sticky feeling was perceived was rates as 2, and the cloth on which the sticky feeling was perceived and there was problems in using the cloth was rates as 1.

(Durability Test)

Each of the cloths prepared in Examples 1 and 8 to 12 and Comparative Example 12 was put in a 2 L beaker containing 1.5 L of purified water, and the content of the beaker was stirred for 10 minutes with a stirrer, and then the purified water was replaced with new purified water and the content was stirred again for 10 minutes. And then, the cloth was dried and the ability of the cloth to suppress an allergen was evaluated by the same manner as described above. Durability was evaluated based on the retention rate of a drug efficacy determined from the following equation.

Retention rate of drug efficacy (%)=(allergen suppression rate of a cloth after wash treatment)/(allergen suppression rate of a cloth without wash treatment)×100

The results of the evaluations are shown in Table 1.

TABLE 1

|  | Allergen suppression rate (%) | Evaluation of feeling | Retention rate of drug efficacy (%) |
| --- | --- | --- | --- |
| Example 1 | 84.3 | 4 | 62.3 |
| Example 2 | 67.1 | 4 |  |
| Example 3 | 65.7 | 4 |  |
| Example 4 | 78.6 | 4 |  |

TABLE 1-continued

| | Allergen suppression rate (%) | Evaluation of feeling | Retention rate of drug efficacy (%) |
|---|---|---|---|
| Example 5 | 92.9 | 4 | |
| Example 6 | 95.7 | 4 | |
| Example 7 | 90 | 4 | |
| Example 8 | 80 | 4 | 93.4 |
| Example 9 | 80 | 4 | 89.4 |
| Example 10 | 74.3 | 4 | 92.8 |
| Example 11 | 68.6 | 4 | 95.1 |
| Example 12 | 87.1 | 3 | 51.3 |
| Example 13 | 55.7 | 4 | |
| Example 14 | 87.3 | 4 | |
| Example 15 | 81.2 | 2 | |
| Example 16 | 61.7 | 4 | |
| Example 17 | 77.8 | 4 | |
| Example 18 | 59.4 | 4 | |
| Example 19 | 44.6 | 4 | |
| Example 20 | 47.9 | 4 | |
| Example 21 | 43.4 | 4 | |
| Comparative Example 1 | 0.7 | 4 | |
| Comparative Example 2 | −2.8 | 4 | |
| Comparative Example 3 | 1.4 | 4 | |
| Comparative Example 4 | −1.4 | 4 | |
| Comparative Example 5 | 2.9 | 4 | |
| Comparative Example 6 | 2.9 | 4 | |
| Comparative Example 7 | 4.3 | 4 | |
| Comparative Example 8 | 14.3 | 4 | |
| Comparative Example 9 | 7.1 | 4 | |
| Comparative Example 10 | 8.6 | 4 | |
| Comparative Example 11 | 13.7 | 4 | |
| Comparative Example 12 | 75.7 | 1 | 18.8 |
| Comparative Example 13 | 2.9 | 4 | |
| Comparative Example 14 | 12.9 | 4 | |
| Comparative Example 15 | −4.8 | 4 | |
| Comparative Example 16 | 5.7 | 4 | |

From Table 1, it is found that in the cloths made of allergen-suppression processed fiber prepared in Examples, the amount of the allergen which had been at a high level immediately after preparing the sample was reduced by a large amount after being left standing for 15 hours in a thermo-hygrostat.

On the other hand, effects of suppressing an allergen were hardly found in the cloths prepared in Comparative Examples, which were not subjected to the allergen-suppression process.

INDUSTRIAL APPLICABILITY

The allergen suppressor and the allergen-suppression processed fiber of the present invention can reduce allergens in a life space under the moisture in daily life when this allergen suppressor or this fiber is used for bedclothes, carpets, sofas, curtains or the like, and in the allergen-suppression processed fiber, there is not a risk that drugs enter the body and even patients suffering from allergic diseases can enjoy comfortable life without causing allergic symptoms because this fiber itself is subjected to the allergen-suppression process.

The invention claimed is:

1. An allergen suppressor,
which contains a hydrophilic polymer component wherein said hydrophilic polymer component comprises a combination of polyethylene glycol and sodium polyacrylate and a water-insoluble polymer comprising poly-p-vinyl phenol, wherein said poly-p-vinyl phenol is a component suppressing an allergen.

2. The allergen suppressor according to claim 1,
wherein the hydrophilic polymer component is mixed in proportions of 40 to 1000 weight % with respect to 100 weight % of the component suppressing an allergen.

3. An allergen-suppression processed fiber,
which is processed with the allergen suppressor according to claim 1.

4. A method of producing an allergen-suppression processed fiber, which comprises processing a fiber with the allergen suppressor according to claim 1, and insolubilizing a hydrophilic polymer.

5. A method of producing an allergen-suppression processed fiber, which comprises processing a fiber with the allergen suppressor according to claim 1, and chemically combining with or post-fixing said allergen suppressor to said fiber.

* * * * *